United States Patent [19]

Anderson et al.

[11] Patent Number: 4,986,823
[45] Date of Patent: Jan. 22, 1991

[54] URINARY AID FOR HUMAN FEMALES

[76] Inventors: Verne M. Anderson, 6218 N. Harlem; Laurence A. Levine, 1903 N. Hudson Ave., both of Chicago, Ill. 60614

[21] Appl. No.: 348,278

[22] Filed: May 5, 1989

[51] Int. Cl.$^5$ .............................................. A61F 5/44
[52] U.S. Cl. .................................................. 604/329
[58] Field of Search ............... 128/761; 604/328–331; 4/144.2–144.4; 600/29, 30

[56] References Cited

U.S. PATENT DOCUMENTS

| | | | |
|---|---|---|---|
| 59,999 | 11/1866 | Harding. | |
| 2,574,767 | 11/1951 | Stubbs | 128/127 |
| 3,347,238 | 10/1967 | Gresham | 128/295 |
| 3,661,155 | 5/1972 | Lindan | 128/295 |
| 3,776,235 | 12/1973 | Ratcliffe et al. | 128/295 |
| 4,023,560 | 5/1977 | Cade et al. | 128/295 |
| 4,246,901 | 1/1981 | Michaud | 128/295 |
| 4,681,572 | 7/1987 | Tokorz et al. | 604/329 |
| 4,846,818 | 7/1989 | Keldahl | 128/761 |
| 4,920,986 | 5/1990 | Biswas. | |

FOREIGN PATENT DOCUMENTS 2090144  7/1982  United Kingdom ................ 604/331

OTHER PUBLICATIONS

Hollister Incorporated Brochure "Introducing the Hollister Female Urinary Incontinence System" copyright 1988.

Primary Examiner—David J. Isabella
Attorney, Agent, or Firm—Hill, Van Santen, Steadman & Simpson

[57] ABSTRACT

A urinary device for human females includes a body of flexible material having a pair of first and second angularly related limbs for insertion into the vagina and a collector extending externally of the vagina with a central opening over the urethral meatus. A collection tube for guiding urine away from the body is attached to the collector. An applicator is provided for some embodiments, while other embodiments are shaped for manual insertion. Various shapes and angles of the body are shown as are different angles of the collection tubes.

36 Claims, 2 Drawing Sheets

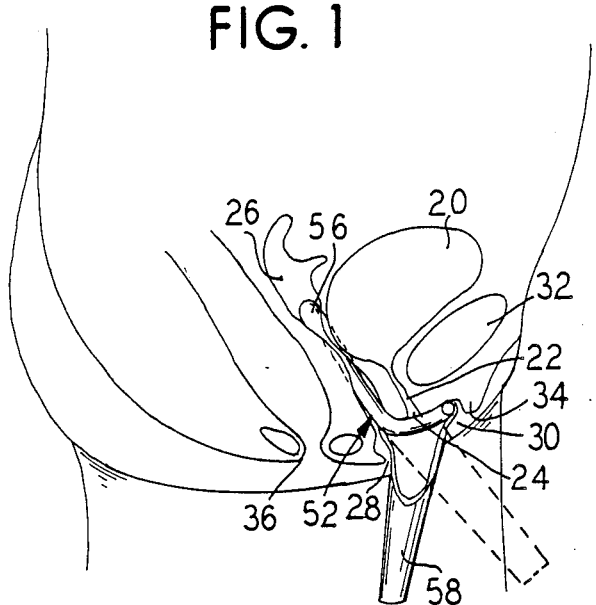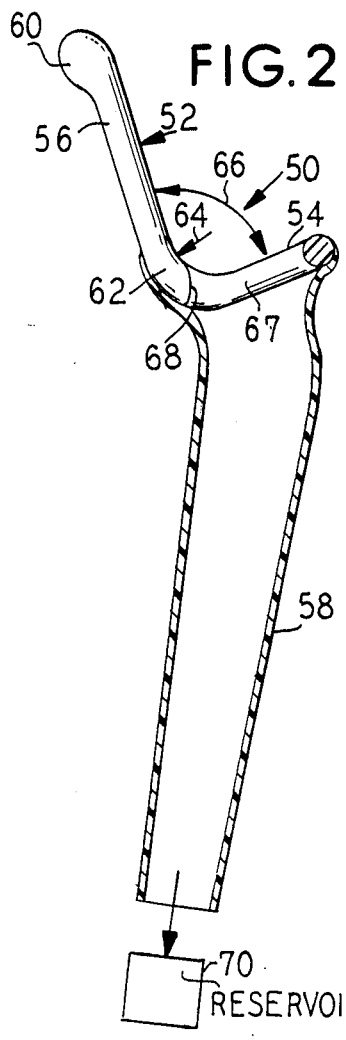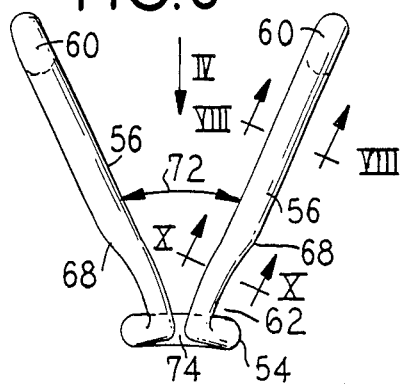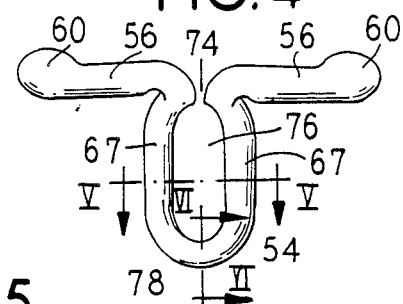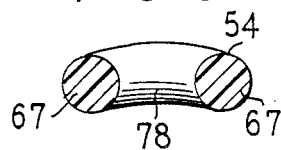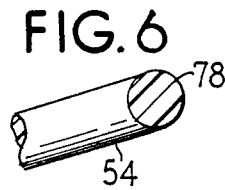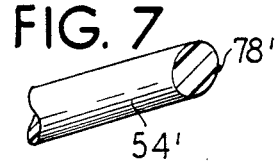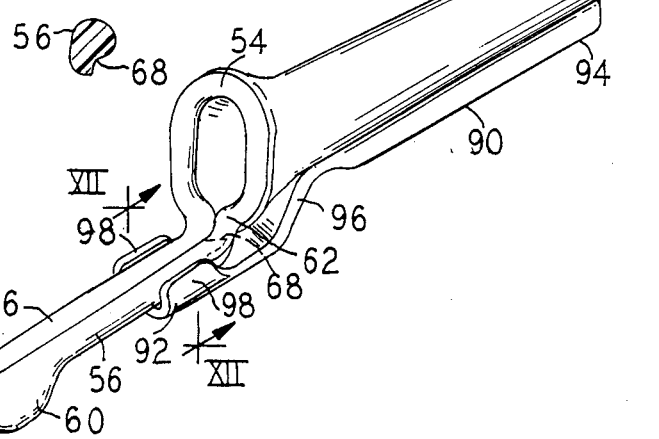

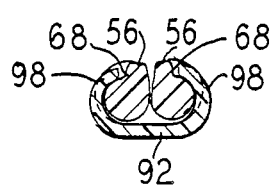
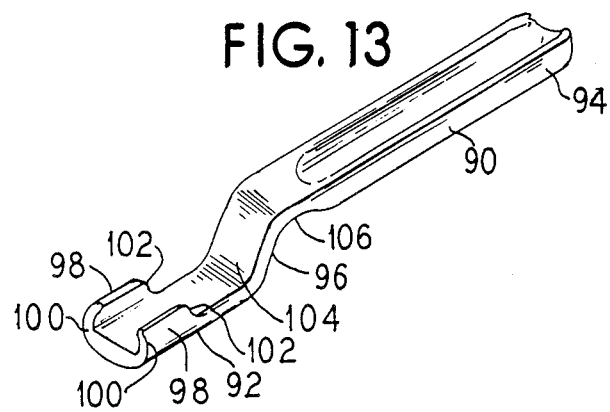
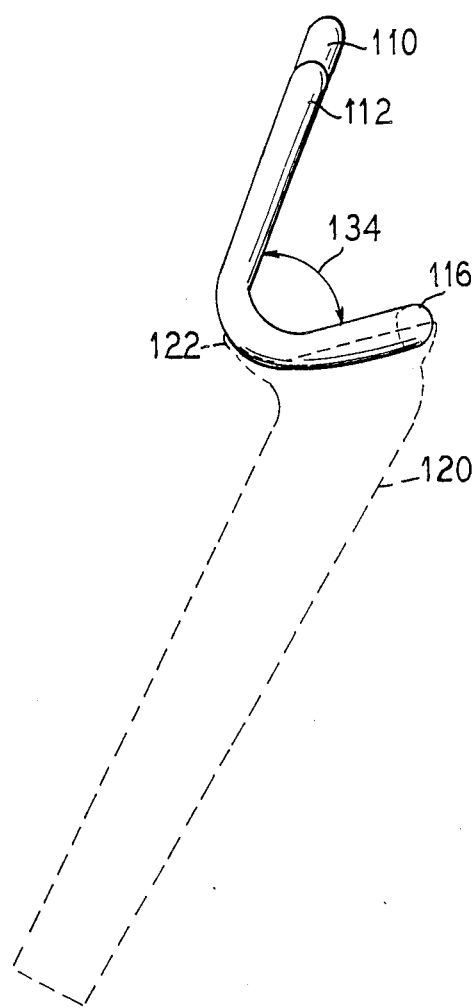
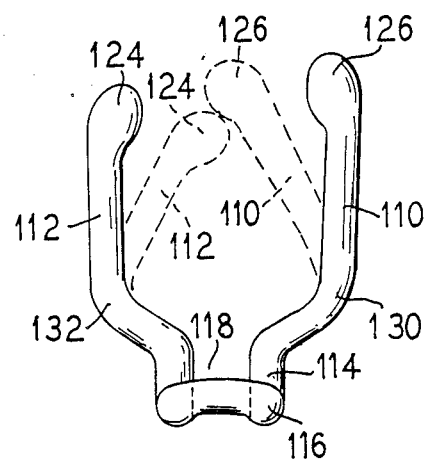
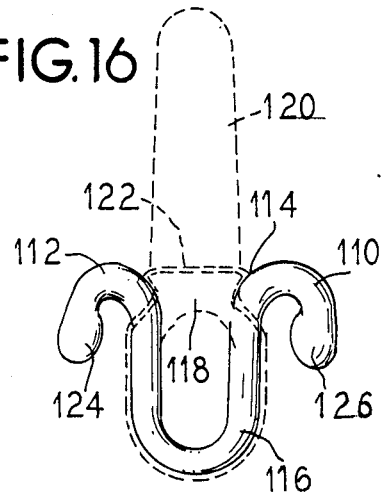

ns of the device as well. Dur-

URINARY AID FOR HUMAN FEMALES

BACKGROUND OF THE INVENTION

1. Field of the Invention

The present invention relates generally to a device for directing a flow of urine from a human female and, more particularly, to a urine collecting device supported by intravaginally extending portions.

2. Description of the Related Art

It is desirable in many situations to be able to direct and collect urine from a human female. For example, hospitalized patients, and particularly bed-ridden patients, such as those in traction, require periodic emptying of the bladder. Females are often in situations where a restroom break is either inconvenient or impossible, such as when working as aircraft pilots and long distance drivers, military personnel in a combat situation, and in space travel and particularly when in a space suit. Furthermore, incontinent females are presented with problems in collecting urine flow.

The simplest and most direct approach to these problems is an internal catheter extending into the urethra. This, however, is uncomfortable and may lead to irritation and is not acceptable in long term use.

Various externally and internally applied apparatus have been proposed including, for example, a female urinary incontinence device disclosed in U.S. Pat. No. 3,661,155 including a pessary-like support connected to a deformable loop extending outwardly from the support to which a flexible container is removably secured. The support portion is a spring diaphragm ring covered with a latex covering and the deformable loop is a malleable wire covered with a coating.

In U.S. Pat. No. 3,347,238 is disclosed a urine collecting device with a resilient elongated vaginal insert providing support for a urine collecting receptacle connected to a drain tube. The resilient member is provided with a degree of stiffness and strength by a metal or plastic resin rod extending therewithin.

A urine collecting device is disclosed in U.S. Pat. No. 4,246,901 which includes a body of wicking material adjacent a urine collection chamber and preferably includes a vaginal insert to position the device and hold it in place.

A portable female urinal is disclosed in U.S. Pat. No. 3,776,235 which includes a collection container formed with a retaining member which is worn internally. Two drain tube openings are also included. The device is supported by a garment or by straps and may include a ring pessary.

It would be an improvement in the art to provide a comfortable, positively positioned urine collecting device for use by females.

SUMMARY OF THE INVENTION

An object of the present invention is to collect urine from a human female without leakage and without discomfort or irritation.

Another object of the invention is to collect urine from a human female in a standing, sitting or reclining position.

A further object of the invention is to provide a urine collecting device which is self-supported by a vaginal insert and which resists expulsion and movement out of position.

These and other objects and advantages of the invention are provided in a urinary aid for human females having a body of flexible material including first and second limbs lying at an angle to one another when in a relaxed position, a collector having a central opening and lying in a plane distinct from the plane of the first and second limbs, and a neck region connecting the first and second limbs to the collector. A collection tube is preferably connected to the collector. In some embodiments, the apparatus is used with an applicator for inserting the device into position. The limbs of the device flex inwardly toward one another, not only for comfort but to provide easy insertion of the device as well. During insertion, the limbs are moved together, either by hand or with an applicator, to provide a small insertion profile. The limbs are inserted through the vaginal orifice and the limbs are released, preferably slowly. This permits the limbs to spread apart to a deployment angle within the vagina. In the deployment angle, the limbs resist inadvertent removal due to their spring-like action and due to the natural muscle tension at the vaginal orifice. The limbs preferably do not stretch or otherwise stress the vaginal tissue, however.

The collector portion of the device remains outside the vagina with the opening held securely over the urethral meatus so that urine flow is directed into the collection tube without mishap. The shape of the neck and the collector insures that the collector opening remains over the opening of the urethra, even during active lifestyle and exercise. For removal of the device, the collector is simply grasped and gently pulled from the body.

The apparatus of the invention fits the female anatomy and its shape and structure uses muscle and tissue to remain in position and resist inadvertent removal. The apparatus is comfortable in use, non-irritating, and resists leaking. The device compensates for various positions in the urethral meatus of different individuals as well as for varying sizes of the vaginal orifice and different relative angles of the vagina. Different embodiments are provided depending upon whether insertion is by using an applicator or by hand. The embodiments designed for use with an applicator include specific features allowing for more comfortable insertion with the applicator.

The applicator provided with the device of the invention is of a size and configuration to aid in determining the anatomical characteristics of the wearer and aid in supplying an embodiment conforming to that individual.

BRIEF DESCRIPTION OF THE DRAWINGS

FIG. 1 is medial cross section of the torso of a human female showing the urogenital system and showing an embodiment of a urinary aid according to the principles of the present invention in position therein;

FIG. 2 is a side elevational view, partially in cross section, of the urinary aid of FIG. 1 including a collection tube mounted at a somewhat different angle;

FIG. 3 is a rear view of the urinary device of FIG. 2 with the collection tube removed;

FIG. 4 is an end elevational view of the device generally in the direction of the arrow IV in FIG. 3;

FIG. 5 is a cross section of the collector along V—V of FIG. 4;

FIG. 6 is a cross section of the collector along VI—VI of FIG. 4;

FIG. 7 is a cross section of the collector along the same direction as shown in FIG. 6 of an alternate embodiment of the urinary device;

FIG. 8 is a cross section through a limb of the device shown in FIG. 3 along line VIII—VIII;

FIG. 9 is a cross section of a limb in the same direction as FIG. 8 of an alternate embodiment of the invention;

FIG. 10 is a cross section along line X—X of FIG. 3 showing a deployment notch in a limb of the device;

FIG. 11 is a perspective view of an embodiment the present urinary device mounted on a applicator and ready for insertion;

FIG. 12 is a cross section along line XII—XII of FIG. 11 showing the applicator holding the limbs of the device;

FIG. 13 is a perspective view of the applicator according to the present invention;

FIG. 14 is a side elevational view of another embodiment of the urinary device of the present invention;

FIG. 15 is a front elevational view of the device of FIG. 14 shown without the collection tube; and FIG. 16 is a top view of the urinary device of FIG. 14.

DESCRIPTION OF THE PREFERRED EMBODIMENTS

Referring first to FIG. 1, the urogenital system of the human female is shown in cross section including the bladder 20 from which extends the urethra 22 to the urethral outlet or urethral meatus 24. Immediately rearwardly of the urethra 22 is the vagina 26 with the vaginal orifice 28. Surrounding the vaginal orifice 28 and urethral meatus 24 are the minor and major labia 30. The pubic symphysis and public bones 32 lie anterior to the urethra 22 and the glans of the clitoris 34 is anterior of the urethral meatus 24. Posterior to the vaginal orifice 28 is the anus 36. The bladder 20 is shown in the full condition, pressing downwardly on the vagina 26.

The urinary aid or device 50 of the present invention is shown in place in the view of FIG. 1. The device 50 includes a body 52 having a collector 54 surrounding the urethral meatus 24 and a pair of limbs 56 extending internally of the vagina 26 through the vaginal orifice 28. A collection tube 58 is connected to the collector 54. As can be seen, the full bladder lies between the limbs 56 of the device 50.

In FIG. 2 is shown the device 50 in greater detail, including the body 52 connected to the collection tube 58. The limbs 56, only one of which is visible in FIG. 2 each include a bulb 60 at the free end thereof which is enlarged relative to the diameter of the limbs 56 to prevent injury from the relatively smaller diameter limbs 56. Other shapes and positions of bulbs are also contemplated. In the embodiment shown in FIG. 2, the bulbs 60 are each directed toward the rear relative to the collector 54.

The limbs 56 in the first embodiment are straight, opposite their free end, and extend to a neck 62 which connects the limbs 56 to the collector 54. The neck 62 has an internal radius of curvature 64 which provides a smooth transition between the collector 54 and the limbs 56. The radius of curvature 64 enables the device to rock about the tissue surrounding the pubic bones 32 without dislodging the device from its position. The neck 62 also holds the collector 54 at a predetermined comfort angle 66 relative to the limbs 56. In the illustrated embodiment, the comfort angle 66 is approximately 90 degrees, although greater or lesser angles are also contemplated. The comfort angle 66 is varied depending upon the angular relationship of the vagina 26 to the tissue surrounding the urethral meatus 24.

The sides of the collector 54 extending to the neck region 62 form torsion members 67 which act as torsion springs when the limbs 56 are moved toward and away from one another. The torsion members 67 are of a defined cross section to provide a predetermined spring force. The size of the torsion members 67 may vary with the length of the limbs 56 or the spring force of the material. The limbs 56 of some embodiments include a deployment notch 68 for use with an applicator, as will be discussed in conjunction with FIGS. 10 through 13.

The collection tube 58 may be of a variety of shapes, sizes and configurations and may be either permanently or temporarily affixed to the collector 54 of the device. As can be seen by comparing FIGS. 1 and 2, the angle of the collection tube 58 may be varied considerably. A further possibility for the collection tube angle is shown in FIG. 14. The collection tube 58 is a hollow flexible, preferably rubber tube through which urine drains from the collector to a reservoir means 70. The angle of the tube 58 depends upon the primary position of the individual wearing the present device. For example, the angle of the tube 58 shown in FIG. 1 is useful for an individual in a sitting position, such as in a wheel chair, or in the standing position. The tube angle illustrated in FIG. 2 is primarily for use while standing. The tube angle shown in FIG. 14 is angled severely to the rear and is used for an individual who is reclining, such as a bed-ridden patient.

The reservoir 70 into which the collection tube 58 drains may be one of the well known collecting bags for incontinence devices or may be a bed pan or other receptacle. Since the device permits the female to stand while urinating, no special receptacle is required.

In the bottom view of FIG. 3 can be seen the two limbs 56 lying at a deployment angle 72 when the torsion members 67 are not under stress. The deployment angle 72 conforms to the angle formed by the vaginal tissues adjacent the vaginal orifice 28. The deployment angle 72 is of a dimension such that no stretching of the vaginal tissues occur. In one embodiment the deployment angle 72 is 50 degrees.

As can be seen in FIG. 3, the neck 62 which connects the collector 54 to the limbs 56 is of smaller diameter than the collector 54. This permits the neck 62 to pass through the vaginal orifice 28 without irritation. The portions of the limbs 56 at the neck 62 lie immediately adjacent one other, yet are still spaced by a small gap 74 to permit twisting of the torsion members 67. The size of the gap 74 may vary considerably, as will be seen. The deployment notch 68 is on the outside surfaces of the limbs 56 and tapers smoothly to the neck 62. The smooth taper eases the removal of the device from the applicator so that the limbs 56 open slowly.

In FIG. 4, the collector 54 has a central opening 76 which is placed in registration with the urethral meatus 24. In the illustrated example, the collector 54 is shaped to provide an elongated oval shaped central opening 56. Round and other shapes of openings are also possible. The central opening 76 is nearly closed at the gap 74 in the illustrated embodiment.

Various cross sections are shown in FIGS. 5 through 10 of different portions and embodiments of the device. In FIG. 5, a cross section through the torsion members 67 forming the sides of the collector 54 reveals that the torsion members 67 are circular in cross section to provide a spring action without weakening the device. In FIG. 6, a cross section through an end 78 of the collector 54 is likewise circular in cross section. As an alternate embodiment shown in FIG. 7, the section through the end 78 is oval. To strengthen the device and prevent unwanted bending, the end 78 may be of a larger diameter than the torsion members 67.

FIGS. 8 and 9 show two embodiments of the limbs 56. In the embodiment of FIG. 8, each of the limbs 56 is circular in cross section. The embodiment of FIG. 9 shows a limb 56 having a somewhat "D"-shaped section with a flattened wall 80 directed toward the opposing limb 56 so that when the limbs 56 are moved together, the flattened walls 80 lie adjacent one another. This aids in the prevention of pinching of tissue during insertion of the device.

In FIG. 10 can be seen the deployment notch 68 in a limb 56 which engages a fitting of an applicator, as discussed hereinafter.

The shaped of the deployment notch 68 depends upon the applicator used. The torsion members 67 urge the limbs 56 into the deployment angle 72 shown in FIG. 3, which holds the device in place as the result of the natural muscle tension at the vaginal orifice 28. The angled legs 56 also permit the full bladder to move to its natural position as shown in FIG. 1 without discomfort. However, insertion of the device requires that the angled legs 56 be moved toward one another to present a smaller profile for insertion through the vaginal orifice. This can either be done by hand or with an applicator 90 as shown mounted on the device 50 in FIG. 11. The applicator 90 includes a fitting or shoe 92 which grips the opposite sides of the limbs 56 to hold them together for insertion. A handle 94 is connected to the fitting 92 by a linkage 96. As can be seen, the fitting 92 includes a pair of flanges 98 which slide over the deployment notch 68 at the neck end of the limbs 56. To use the applicator 90, the limbs 56 and fitting 92 are inserted into the vagina and the thumb or finger is used to hold the collector 54 while the applicator 10 is withdrawn. The fitting 92 thereby slides off of the device 50 and the shaped shoulders on the deployment notch permit the limbs 56 to move outward slowly rather than abruptly In the cross section of FIG. 12, the curved flanges 98 of the fitting 92 are shown engaging the deployment notches 68 of the limbs 56. The flanges 98 conform closely to the shape of the limbs 56 to avoid the chance of pinching, while holding the limbs 56 in the insertion position.

With reference to FIG. 13, the applicator 90 is formed to reduce as much as possible the risk of the discomfort or injury during insertion and use of the present device. The flanges 98 gently curve upward in a rounded lead radius 100 and end in a gentle trailing radius 102 so that sharp corners are not present. The linkage 96 has a primary curve 104 conforming to the angle of the device and a secondary curve 106 depending upon the tube angle and the application position desired. The handle 94 is preferably relieved to fit the user's hand and to provide a uniform cross section to reduce molding problems. It is contemplated that a two part, hinged applicator may also be used, such applicator being similar to a scissors but with limb grasping fittings on the arms.

In addition to the use of the applicator 90 for insertion of the urinary device 50, the applicator as shown is also useful as a diagnostic device. The length of the handle 94 corresponds generally to the length of the limbs 56 so that the handle 94 of the applicator 90 may be used to determine whether the vagina has the necessary depth for use of the present device. If not, a model with shorter limbs may be chosen. The width of the handle corresponds to the width of one embodiment of the device at the neck and so may be used to determine whether the vaginal orifice is large enough to accommodate such embodiment or whether a narrower type embodiment must be used.

The material of which the urinary device is formed is preferably a medically acceptable plastic, and the tube 58 is of a material such as RTV Silicone. A solid plastic body 52 is preferred to avoid the risk inherent in a coated metal version. Of course, any appropriate material will do. The applicator may be formed of any suitable material including nylon or styrene. The body 52 of the device is preferably injection molded and the silicon rubber tuber 58 is permanently bonded to it.

The foregoing device provides exemplary performance in many situations and for many different individuals. However, occasionally, due to the angle of the vagina and the position of the vaginal orifice relative to the urethral meatus, the constricted neck 62 of the foregoing device contacts and irritates the urethral meatus which provides discomfort and aggravates an incontinence problem. Therefore, another embodiment of apparatus shown in FIGS. 14 through 16 is provided having limbs 110 and 112 spaced relatively farther apart at a neck 114 where they join a collector 116. A urethral clearance 118 is, thus, provided. In this embodiment, the relatively softer collection tube 120 extends across the urethral space 118 to form a bridge 122 to prevent leakage. This model requires that the wearer be able to accommodate the wider neck 114 extending through the vaginal orifice comfortably.

The embodiment of FIGS. 14 through 16 includes features for manual insertion so that no deployment groove for an applicator is provided. Instead, the first limb 110 is slightly longer than the second limb 112 and bulbs 124 and 126 at the free ends thereof are directed inwardly. As shown in dotted outline, when the limbs 110 and 112 are moved toward one another, the bulb 126 overlies the bulb 124 so that a single surface is presented at the vaginal orifice to ease insertion.

Referring to FIG. 15, the limbs 110 and 112 are bent at bends 130 and 132 rather than being straight as in the previous embodiments. The bends 130 and 132 in the limbs 110 and 112 aid in insertion of the device by reducing the degree the device must be collapsed to allow insert. It is contemplated that the limbs 56 could be reduced in cross section sufficiently that they would be rendered flexible enough to be brought together for insertion. An embodiment so configured would not rely on the bending of the sides of the collector as torque members.

A further difference between this embodiment and the foregoing embodiments is illustrated in FIG. 14. In particular, an angle 134 between the collector 116 and the limbs 110 and 112 is less than 90 degrees to accommodate individuals with a somewhat different vaginal angle.

By disclosing different embodiments, it is not intended to suggest that only these embodiments are possible. Instead, any feature from one embodiment can be incorporated in the other embodiment to fit the needs of the individual wearer. Thus, the angled limbs can be included on an embodiment with a narrow neck, or the limbs of different length used on an applicator-insertable version. As will be appreciated by those of skill in the art, the invention as described herein may also include various modifications in shape, size and configuration over that illustrated to suit the individual wearer and the position and use to which the device will be put.

The configuration of the disclosed embodiments permits the limbs to be moved toward one another for ease of insertion and thereafter to open to the deployment angle to hold the device in place. The spaced arms, which are biased to the deployment angle, insure that the device is not dislodged or moved out of position. The device remains in a positive position due to the angled limbs engaging the lower portion of the vaginal walls. Muscle contractions of the various muscle groups around the vaginal orifice, anus and bladder do not dislodge or dislocate the device since the torsion spring loaded limbs ride along with the tissue and only cause some rocking of the device about the pubic symphysis or pubic bones.

The collector portion is urged against the region surrounding the urethral meatus between the labia minor to provide a seal which prevents leakage of urine as an emergent stream of urine leaves the urethra and flows through the tube and away from the body. The device can be used for short term wear, although it is comfortable enough for longer periods of wear. It is easily removed from the body by grasping the collector portion and pulling which causes the limbs to fold inwardly and pass through the vaginal orifice.

Although other modifications and changes may be suggested by those skilled in the art, it is the intention of the inventors to embody within the patent warranted hereon all changes and modifications as reasonably and properly come within the scope of their contribution to the art.

We claim:

1. A urinary aid to be worn by human females, comprising:
   a body of flexible material including:
      first and second limbs configured to be worn intravaginally, said limbs subtending an acute angle to one another when in a relaxed position, each of said first and second limbs having a bulbuous free end, said free ends being unconnected to form an open end of said body, said first and second limbs lying generally in a first plane,
      a collector lying in a plane distinct from the first plane, said collector having a central opening configured to be positioned about the urethral meatus when said limbs are positioned intravaginally; and
      a hollow collection tube having an opening, said hollow collection tube being connected to said collector in a position so that said open end of said tube is in registration with said central opening in said collector.

2. A urinary aid as claimed in claim 1, wherein said first and second limbs are each generally straight.

3. A urinary aid as claimed in claim 1, wherein said first and second limbs each include a bend.

4. A urinary aid as claimed in claim 1, wherein said collection tube is bonded to said collector.

5. A urinary aid as claimed in claim 1, wherein said first and second limbs are connected to a base portion of said collector to form a neck region.

6. A urinary aid as claimed in claim 5, wherein said limbs lie adjacent to one another at said neck region.

7. A urinary aid as claimed in claim 6, wherein said central opening is of an oval shape.

8. A urinary aid as claimed in claim 5, wherein said limbs are spaced apart from one another by a predetermined distance at said neck region so that a channel is formed therebetween, said channel extending to said central opening in said collector.

9. A urinary aid as claimed in claim 5, wherein said neck region curves between said first and second limbs lying in said first plane and said collector lying in said plane distinct from said first plane.

10. A urinary aid for human females, comprising:
    a body of flexible material including:
       first and second limbs lying at an angle to one another when in a relaxed position, each of said first and second limbs having a free end with a bulb, said first and second limbs lying generally in a first plane, each of said first and second limbs having a deployment notch at an end opposite said free end;
       a collector lying in a plane distinct from the plane of said first and second limbs, said collector having a central opening;
       first and second torsion portions connecting respective ones of said first and second limbs to said collector, said torsion portions undergoing flexing as said first and second limbs are moved toward one another; and
    a collection tube connectable to said collector in a position so that an open end of said tube is in registration with said central opening in said collector.

11. A urinary aid as claimed in claim 10, further comprising:
    an applicator having a fitting for engagement over said deployment notches and onto said first and second limbs when said limbs are moved toward one another to an insertion position, said fitting of said applicator retaining said first and second limbs in said insertion position and being selectively removable from said first and second limbs to permit said limbs to move to said relaxed position, and
    a handle attached to said fitting of said applicator.

12. A urinary aid as claimed in claim 11, wherein said handle is of a length corresponding to a length of said first and second limbs.

13. A urinary aid as claimed in claim 12, wherein a neck region is provided between said collector and said limbs, and said handle of said applicator has a width corresponding to a width of said neck region.

14. A urinary aid as claimed in claim 1, wherein said bulbuous free ends of said first and second limbs extend generally rearwardly relative to said collector.

15. A urinary aid as claimed in claim 1, wherein said first and second limbs are of substantially the same length.

16. A urinary aid for human females, comprising:
    a body of flexible material including:
       first and second limbs lying at an angle to one another when in a relaxed position, each of said first and second limbs having a free end with a bulb, said first and second limbs lying generally in a first plane, said first and second limbs being of mutually different lengths and said bulbs at the free ends of said limbs being directed inwardly toward one another to overlap when said first and second limbs are moved together into an insertion position;
       a collector lying in a plane distinct from the plane of said first and second limbs, said collector having a central opening;

first and second torsion portions connecting respective ones of said first and second limbs to said collector, said torsion portions undergoing flexing as said first and second limbs are moved toward one another; and a collection tube connectable to said collector in a position so that an open end of said tube is in registration with said central opening in said collector.

17. A urinary aid as claimed in claim 1, wherein said first and second limbs are round in cross section.

18. A urinary aid as claimed in claim 1, wherein said first and second limbs each have a D-shaped cross section with flattened portions oriented to lie adjacent one another when said limbs are moved toward one another into an insertion position.

19. A urinary device for use by a human female, comprising:

a collector having an opening configured for placement surrounding the urethral meatus of the human female in generally sealing engagement;

a hollow tube having an open end, said hollow tube extending from said collector for carrying urine away from the urethral meatus; and means for holding said collector in sealing engagement surrounding the urethral meatus, said means including:

first and second elongated limbs having first ends connected to said collector and having second opposite ends being unconnected free ends to form an open end of said holding means configured for extending into the vagina of the human female, said limbs being movable between an insertion position characterized by said first and second limbs lying generally along side one another and a deployment position characterized by said first and second limbs subtending an acute angle relative to one another; and means for biasing said first and second limbs toward said deployment position.

20. A urinary device as claimed in claim 19, wherein said collector and said means for holding are molded in one piece.

21. A urinary device as claimed in claim 19, wherein said collector and said means for holding are joined to one another by a neck region of a predetermined radius of curvature and a predetermined width.

22. A urinary device as claimed in claim 21, wherein said predetermined width of said neck region is less than a width of said collector.

23. A urinary device as claimed in claim 21, wherein said predetermined width of said neck region is substantially the same as a width of said collector.

24. A urinary device as claimed in claim 19, wherein said first and second elongated limbs each have an enlarged flattened bulb at a free end thereof.

25. A urinary device for use by a human female, comprising:

a rod of flexible material having a middle extent forming a collector portion with a central opening configured for disposition over the urethral meatus of the human female, opposite end portions of said rod forming limbs subtending an acute angle relative to one another when in a relaxed position, said limbs being flexibly movable toward one another to reduce the angle between said limbs to achieve an insertion position of said limbs configured for insertion into the vagina of the human female, said limbs being biased angularly outwardly relative to one another once inside the vagina to urge said collector into sealing engagement against the region around the urethral meatus;

a neck region between said collector portion and said limbs, said neck region defining a curve to permit movement of said device as the human female moves to maintain a substantially sealing engagement of said collector about the urethral meatus;

a hollow flexible tube connected to said collector portion, said tube having a first open end in fluid communication with said central opening.

26. A urinary device as claimed in claim 25, wherein said flexible tube extends from said collector substantially parallel to a plane defined by said limbs.

27. A urinary device as claimed in claim 25, wherein said flexible tube extends from said collector forwardly of a plane defined by said limbs.

28. A urinary device as claimed in claim 25, wherein said flexible tube extends from said collector rearwardly of a plane defined by said limbs.

29. A urinary device as claimed in claim 24, wherein said enlarged flattened bulbs at said free ends of said first and second elongated limbs are directed toward one another.

30. A urinary device as claimed in claim 29, wherein said bulbs overlap when said first and second elongated limbs are moved toward one another.

31. A urinary aid as claimed in claim 1, further comprising:

an applicator having an engaging portion mountable in an engaging relationship with said first and second limbs to hold said first and second limbs at an angle less than said acute angle.

32. A urinary aid as claimed in claim 5, wherein said neck region is at least as wide as said collector.

33. A urinary device as claimed in claim 25, wherein said limbs have free ends forming an open end of said device.

34. A urinary device as claimed in claim 19, further comprising:

an applicator having a limb engaging portion mountable on said first and second elongated limbs to hold said limbs generally in said insertion position, said applicator being selectively removable from said limbs to enable said limbs to move to said deployment position.

35. A urinary device as claimed in claim 25, further comprising:

an applicator connectable to said rod to retain said limbs generally in the insertion position, said applicator selectively enabling said limbs to move angularly away from one another.

36. A urinary device as claimed in claim 19, wherein said collector lies in a plane.

* * * * *